United States Patent [19]

Nakai et al.

[11] Patent Number: 5,723,117
[45] Date of Patent: Mar. 3, 1998

[54] USE OF INTERLEUKIN-1 (IL-1) TO INHIBIT DEVELOPMENT OF HEPATITIS

[75] Inventors: Satoru Nakai, Tokushima; Seiji Akamatsu, Naruto; Yoshihiro Masui, Tokushima; Tsutomu Nishida, Naruto; Takashi Kamogashira, Tokushima; Yoshikatu Hirai, Suita, all of Japan

[73] Assignee: Otsuka Pharmaceutical Co., Ltd., Tokyo, Japan

[21] Appl. No.: 139,862

[22] Filed: Oct. 22, 1993

Related U.S. Application Data

[62] Division of Ser. No. 839,770, filed as PCT/JP91/01067, Aug. 9, 1991 published as WO92/02236, Feb. 20, 1992, abandoned.

[30] Foreign Application Priority Data

Aug. 10, 1990 [JP] Japan ................... 2-212941

[51] Int. Cl.$^6$ ................................. A61K 38/20
[52] U.S. Cl. ........................ 424/85.2; 435/69.52
[58] Field of Search ................ 424/85.2; 435/69.52

[56] References Cited

U.S. PATENT DOCUMENTS

| | | | |
|---|---|---|---|
| 5,008,374 | 4/1991 | Nakai et al. | 530/351 |
| 5,017,692 | 5/1991 | Zurawski et al. | 530/351 |
| 5,120,534 | 6/1992 | Hirai et al. | 424/85.2 |

FOREIGN PATENT DOCUMENTS

| | | | |
|---|---|---|---|
| 187991 | 7/1986 | European Pat. Off. | C12N 15/00 |
| 237073 | 9/1987 | European Pat. Off. | C07K 13/00 |
| 237967 | 9/1987 | European Pat. Off. | C07K 13/00 |
| 0352816 | 1/1990 | European Pat. Off. | |
| 2157231 | 6/1990 | Japan | |

OTHER PUBLICATIONS

Müller, C. et al. (1989) *Arch. Dis. Childhood* 64: 205–210.
Roh, M. S., et al. (1986) *Metabolism* 35: 419–24.
Schilsky, M. L. et al. (1994) *Am. J. Physiol.* G907–G913.
Lillquist, J.S., et al. (1988) *J. Immunol.* 141: 1975–81.
Kamogashira, T., et al. (1988) *J. Biochem.* (Tokyo) 104: 837–40.
Zucali, J.R., et al. (1990) *Exp. Hematol.* 18: 1078–82.
Rosenwasser, L. J., et al. (1986) *Proc. Natl. Acad. Sci. USA* 83: 5243–46.
De Chiara, T.M., et al. (1986) *Proc. Natl. Acad. Sci. USA* 83: 8303–07.
Messing et al. *Gene*, 19:269–276 (1982).
Gluzman, *Cell*, 23:175–182 (1981).
Urlaub et al. *Proc. Nat'l Acad. Sci USA*, 77:4216–4220 (1980).
Subramani et al. *Mol. Cell. Biol.*, 1(9):854–864 (1981).
Fumio, *Taisha*, 22:289–298 (1985).
Biochemistry Data Book II, K.k. Tokyo Kagaku Dojin, publisher, pp. 1175–1259 (1980).
Oppenheim et al. *J. Immunol.*, 116:1466–1472 (1976).
Kamogashira et al. *Biochem. Biophys. Res. Comm.*, 150:1106–1114 (1988).
Maniatis et al. *Molecular Cloning*, Cold Spring Harbor Laboratory, p. 366 (1982).
Sakamoto et al. *Hepato–gastroenterol.*, 31:248–253 (1984).
McClain et al. *Life Sci.*, 39:1479–1485 (1986).
Anastassakos et al. *Clin. Exp. Immunol.*, 68:15–22 (1987).
Kakumu et al., *J. Clin. Lab. Immunol.*, 26:113–119 (1988).
Anastassakos et al. *Gastroenterol.*, 94:999–1005 (1988).
Keller et al. *FEMS Microbiol. Immunol.*, 47:87–96 (1988).
Abe et al. *Naika Mook*, 34:1–12 (1987).
Mori et al. Kan.Tan.Sui (Japan), 19(5):905–910 (1989).
Kamata, *General Clinics*, 139(7):1837–1842 (1990).
Hoofnagle et al. *Gastroenterol.*, 95:1318–1325 (1988).
Garcia et al. *Ann. Intern. Med.*, 107:278–285 (1987).
Alexander et al. *J. Med. Virol.*, 21:81–87 (1987).
Kakumu et al. *Hepatology*, 8:487–492 (1988).
Blum et al. *Lancet*, pp. 1153–1155 (Dec. 3, 1977).
Fattovich et al. *Gastroenterol.*, 91:692–696 (1986).
Hoofnagle et al. *Ann. Intern. Med.*, 104:12–17 (1986).
Porres et al. *J. Hepatol.*, 8:351–357 (1989).
Auron et al. *Proc. Nat'l Acad. Sci.*, 81:7907–7911 (1984).
March et al. *Nature*, 315:641–647 (1985).
Furutani et al. *Nucl. Acid Res.*, 13(16): 5869–5882 (1985).
Hunkapiller et al. *Nature*, 310:105–111 (1984).
Mark et al. *Proc. Nat'l Acad. Sci.*, 81:5662–5666 (1984).
Maxam et al. *Meth. Enzym.*, 65:499–560 (1980).
Miyanohara et al. *Proc. Nat'l Acad. Sci USA*, 80:1–5 (1983).
Daniels et al. *J. Hepatol.*, 9(1):s23 (1989).
Ozeki et al. *Int. J. Exp. Path.*, 71:815–821 (1990).
Tovey et al. *Autoimmunity*, 10:297–310 (1991).
Daniels et al, Spontaneous Production of Tumor Nucrosis Factor α and Interleukin-1β During Interferon-α Treatment of Chronic HBV Infection, *The Lancet*, 355:875–877 (1990).
Grantham et al. *Nucl. Acid Res.*, 9:43–74 (1981).

*Primary Examiner*—David L. Fitzgerald
*Attorney, Agent, or Firm*—Sughrue, Mion, Zinn, Macpeak & Seas, PLLC

[57] ABSTRACT

A drug for preventing and curing liver diseases comprising at least one member selected from interleukin-1 and its derivatives as an effective component. The drug meaningfully suppresses GOT and GPT activities in blood which are markers of liver diseases, and also suppresses symptoms such as choloplania.

8 Claims, 2 Drawing Sheets

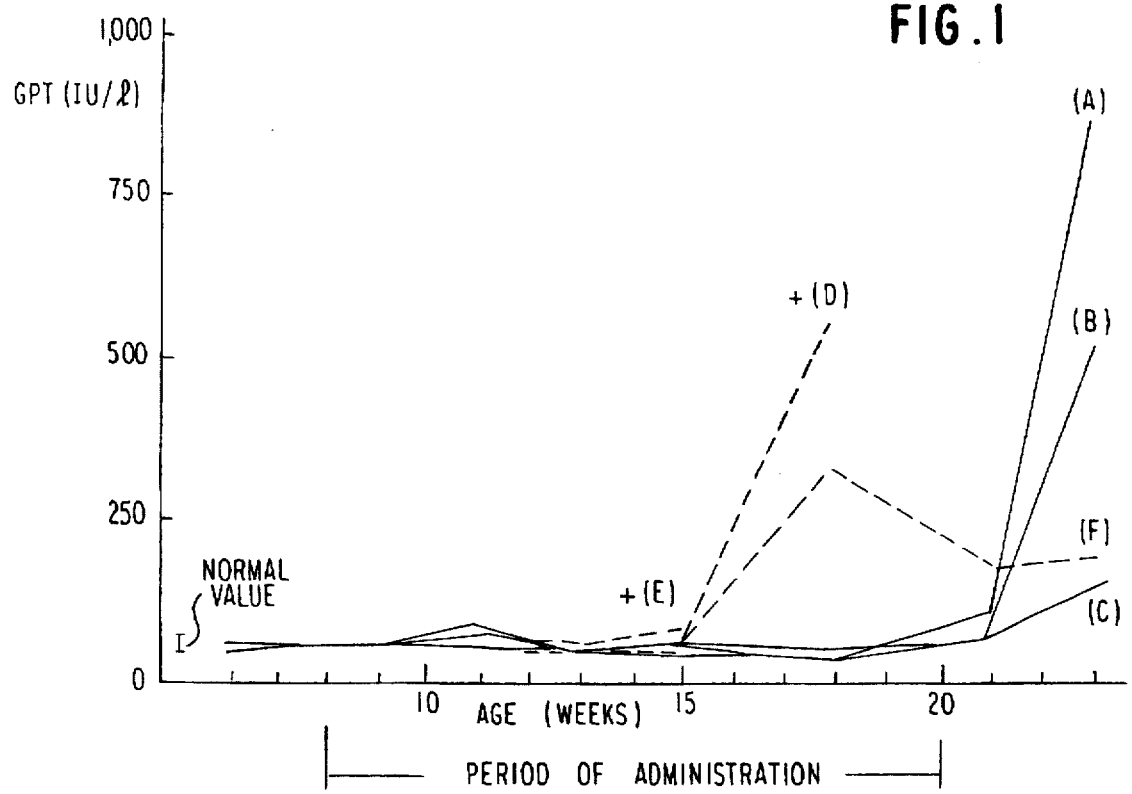
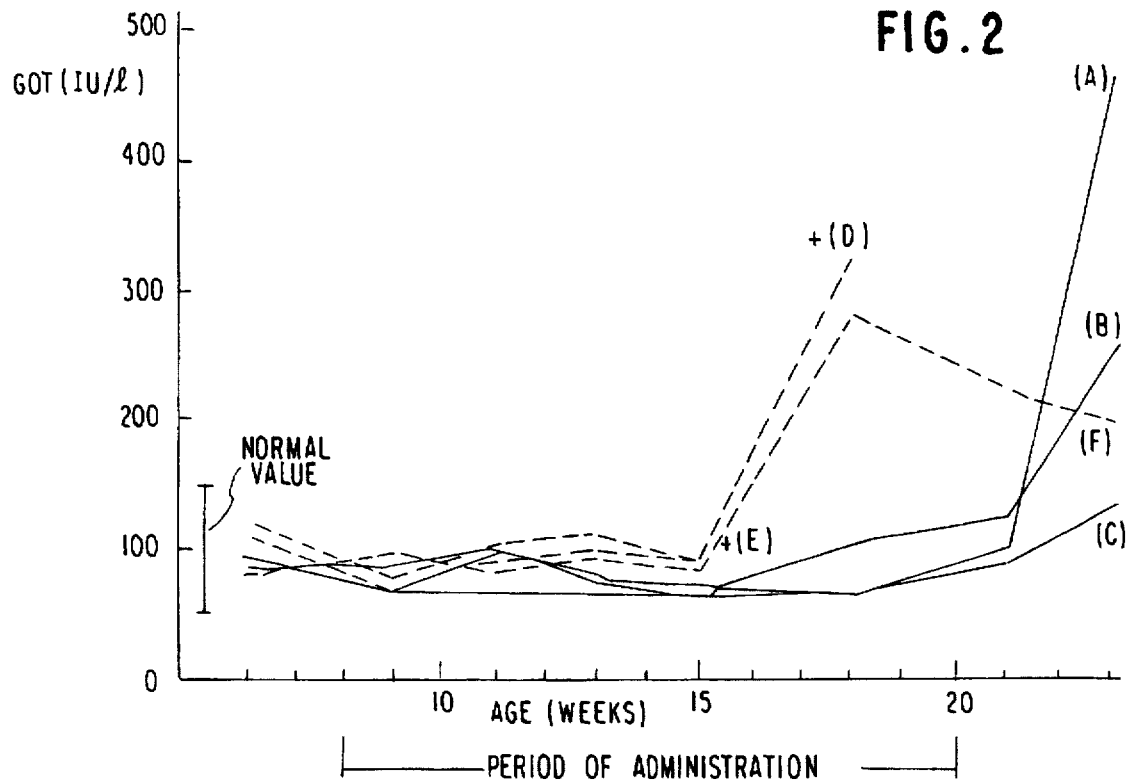

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 159 amino acids
        ( B ) TYPE: amino acid
        ( D ) TOPOLOGY: unknown ( i i ) MOLECULE TYPE: peptide ( v ) FRAGMENT TYPE: N-terminal ( x i ) SEQUENCE DESCRIPTION: SEQ ID NO:1:

```
Ser Ala Pro Phe Ser Phe Leu Ser Asn Val Lys Tyr Asn Phe Met Arg
  1               5                  10                  15
Ile Ile Lys Tyr Glu Phe Ile Leu Asn Asp Ala Leu Asn Gln Ser Ile
             20                  25                  30
Ile Arg Ala Asn Asp Gln Tyr Leu Thr Ala Ala Ala Leu His Asn Leu
         35                  40                  45
Asp Glu Ala Val Lys Phe Asp Met Gly Ala Tyr Lys Ser Ser Lys Asp
     50                  55                  60
Asp Ala Lys Ile Thr Val Ile Leu Arg Ile Ser Lys Thr Gln Leu Tyr
 65                  70                  75                  80
Val Thr Ala Gln Asp Glu Asp Gln Pro Val Leu Leu Lys Glu Met Pro
                 85                  90                  95
Glu Ile Pro Lys Thr Ile Thr Gly Ser Glu Thr Asn Leu Leu Phe Phe
            100                 105                 110
Trp Glu Thr His Gly Thr Lys Asn Tyr Phe Thr Ser Val Ala His Pro
            115                 120                 125
Asn Leu Phe Ile Ala Thr Lys Gln Asp Tyr Trp Val Cys Leu Ala Gly
```

```
                    130                       135                       140
Gly Pro Pro Ser Ile Thr Asp Phe Gln Ile Leu Glu Asn Gln Ala
145                 150                 155
```

(2) INFORMATION FOR SEQ ID NO:2:

(i) SEQUENCE CHARACTERISTICS:
    (A) LENGTH: 159 amino acids
    (B) TYPE: amino acid
    (D) TOPOLOGY: unknown (ii) MOLECULE TYPE: peptide (v) FRAGMENT TYPE: N-terminal (xi) SEQUENCE DESCRIPTION: SEQ ID NO:2:

```
Ser Ala Pro Phe Ser Phe Leu Ser Asn Val Lys Tyr Asn Phe Met Arg
1               5                   10                  15

Ile Ile Lys Tyr Glu Phe Ile Leu Asn Asp Ala Leu Asn Gln Ser Ile
            20                  25                  30

Ile Arg Ala Xaa Asp Gln Tyr Leu Thr Ala Ala Ala Leu His Asn Leu
        35                  40                  45

Asp Glu Ala Val Lys Phe Asp Met Gly Ala Tyr Lys Ser Ser Lys Asp
    50                  55                  60

Asp Ala Lys Ile Thr Val Ile Leu Arg Ile Ser Lys Thr Gln Leu Tyr
65                  70                  75                  80

Val Thr Ala Gln Asp Glu Asp Gln Pro Val Leu Leu Lys Glu Met Pro
                85                  90                  95

Glu Ile Pro Lys Thr Ile Thr Gly Ser Glu Thr Asn Leu Leu Phe Phe
            100                 105                 110

Trp Glu Thr His Gly Thr Lys Asn Tyr Phe Thr Ser Val Ala His Pro
        115                 120                 125

Asn Leu Phe Ile Ala Thr Lys Gln Asp Tyr Trp Val Xaa Leu Ala Gly
    130                 135                 140

Gly Pro Pro Ser Ile Thr Asp Phe Gln Ile Leu Glu Asn Gln Ala
145                 150                 155
```

(2) INFORMATION FOR SEQ ID NO:3:

(i) SEQUENCE CHARACTERISTICS:
    (A) LENGTH: 153 amino acids
    (B) TYPE: amino acid
    (D) TOPOLOGY: unknown (ii) MOLECULE TYPE: peptide (v) FRAGMENT TYPE: N-terminal (xi) SEQUENCE DESCRIPTION: SEQ ID NO:3:

```
Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
            20                  25                  30

Gly Gln Asp Met Glu Gln Gln Val Val Phe Ser Met Ser Phe Val Gln
        35                  40                  45

Gly Glu Glu Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95
```

```
Lys  Arg  Phe  Val  Phe  Asn  Lys  Ile  Glu  Ile  Asn  Asn  Lys  Leu  Glu  Phe
               100                      105                      110

Glu  Ser  Ala  Gln  Phe  Pro  Asn  Trp  Tyr  Ile  Ser  Thr  Ser  Gln  Ala  Glu
               115                 120                      125

Asn  Met  Pro  Val  Phe  Leu  Gly  Gly  Thr  Lys  Gly  Gly  Gln  Asp  Ile  Thr
          130                      135                 140

Asp  Phe  Thr  Met  Gln  Phe  Val  Ser  Ser
145                      150
```

( 2 ) INFORMATION FOR SEQ ID NO:4:

( i ) SEQUENCE CHARACTERISTICS:
        ( A ) LENGTH: 116 amino acids
        ( B ) TYPE: amino acid
        ( D ) TOPOLOGY: unknown ( i i ) MOLECULE TYPE: peptide ( v ) FRAGMENT TYPE: N-terminal ( x i ) SEQUENCE DESCRIPTION: SEQ ID NO:4:

```
Met  Ala  Glu  Val  Pro  Glu  Leu  Ala  Ser  Glu  Met  Met  Ala  Tyr  Tyr  Ser
1                   5                      10                      15

Gly  Asn  Glu  Asp  Asp  Leu  Phe  Phe  Glu  Ala  Asp  Gly  Pro  Lys  Gln  Met
               20                 25                      30

Lys  Cys  Ser  Phe  Gln  Asp  Leu  Asp  Leu  Cys  Pro  Leu  Asp  Gly  Gly  Ile
               35                 40                      45

Gln  Leu  Arg  Ile  Ser  Asp  His  His  Tyr  Ser  Lys  Gly  Phe  Arg  Gln  Ala
          50                 55                      60

Ala  Ser  Val  Val  Val  Ala  Met  Asp  Lys  Leu  Arg  Lys  Met  Leu  Val  Pro
65                       70                      75                            80

Cys  Pro  Gln  Thr  Phe  Gln  Glu  Asn  Asp  Leu  Ser  Thr  Phe  Phe  Pro  Phe
                    85                      90                      95

Ile  Phe  Glu  Glu  Glu  Pro  Ile  Phe  Phe  Asp  Thr  Trp  Asp  Asn  Glu  Ala
               100                      105                      110

Tyr  Val  His  Asp
               115
```

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( x i ) SEQUENCE DESCRIPTION: SEQ ID NO:5:

ACTTTATGGG GATCATCA                                              18

( 2 ) INFORMATION FOR SEQ ID NO:6:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:6:

```
Ser Ala Pro Phe Ser Phe Leu Ser Asn Val Lys Tyr Asn Phe Met Gly
 1               5                  10                 15

Ile Ile Lys Tyr Glu Phe Ile Leu Asn Asp Ala Leu Asn Gln Ser Ile
             20              25                 30

Ile Arg Ala Asp
         35
```

( 2 ) INFORMATION FOR SEQ ID NO:7:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( x i ) SEQUENCE DESCRIPTION: SEQ ID NO:7:

```
AAGGGTATCG ATTATGATGA GGATCATC                                       28
```

( 2 ) INFORMATION FOR SEQ ID NO:8:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:8:

```
Met Met Arg Ile Ile Lys Tyr Glu Phe Ile Leu Asn Asp Ala Leu
 1               5                  10                 15
```

( 2 ) INFORMATION FOR SEQ ID NO:9:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( x i ) SEQUENCE DESCRIPTION: SEQ ID NO:9:

```
AACTAGTACG CAAGTTCACG TAAGGAGGTT TAATATTATG AGAATCATCA AATACG        56
```

( 2 ) INFORMATION FOR SEQ ID NO:10:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( x i ) SEQUENCE DESCRIPTION: SEQ ID NO:10:

```
AATTCGTATT TGATGATTCT CATAATATTA AACCTCCTTA CGTGAACTTG CGTACTAGTT    60
```

( 2 ) INFORMATION FOR SEQ ID NO:11:

( i ) SEQUENCE CHARACTERISTICS:

(A) LENGTH: 23 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:11:

```
Met Arg Ile Ile Lys Tyr Glu Phe Ile Leu Asn Asp Ala Leu Asn Gln
1               5                   10                  15
Ser Ile Ile Arg Ala Asn Asp
            20
```

(2) INFORMATION FOR SEQ ID NO:12:

(i) SEQUENCE CHARACTERISTICS:
(A) LENGTH: 23 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:12:

```
Met Arg Ile Ile Lys Tyr Glu Phe Ile Leu Asn Asp Ala Leu Asn Gln
1               5                   10                  15
Ser Ile Ile Arg Ala Asp Asp
            20
```

(2) INFORMATION FOR SEQ ID NO:13:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: synthetic DNA (xi) SEQUENCE DESCRIPTION: SEQ ID NO:13:

```
GTATCGATAA TGAGAATCAT C                              21
```

(2) INFORMATION FOR SEQ ID NO:14:

(i) SEQUENCE CHARACTERISTICS:
(A) LENGTH: 15 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:14:

```
Met Arg Ile Ile Lys Tyr Glu Phe Ile Leu Asn Asp Ala Leu Asn
1               5                   10                  15
```

(2) INFORMATION FOR SEQ ID NO:15:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: other nucleic acid
(A) DESCRIPTION: synthetic DNA ( x i ) SEQUENCE DESCRIPTION: SEQ ID NO:15:

GAAGATCTTC                                                                                                   10

( 2 ) INFORMATION FOR SEQ ID NO:16:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: synthetic DNA ( x i ) SEQUENCE DESCRIPTION: SEQ ID NO:16:

GCTCTAGAGC                                                                                                   10

USE OF INTERLEUKIN-1 (IL-1) TO INHIBIT DEVELOPMENT OF HEPATITIS

This is a Divisional of application Ser. No. 07/839,770, filed Apr. 9, 1992, now abandoned, which is a national stage (35 U.S.C. § 371) application based on International Application PCT/JP91/01067, filed Aug. 9, 1991 published as WO92/02236, Feb. 20, 1992.

TECHNICAL FIELD

The present invention relates to a drug for preventing and curing the liver disease.

BACKGROUND ART

There are various types of liver diseases, including acute hepatitis, chronic hepatitis, toxic liver injury, hepatic cancer, cirrhotic liver, fatty liver, portal hypertension, and the like. In Japan, patients suffering from acute hepatitis are 180,000 every year. Those suffering from chronic hepatitis, cirrhotic liver, and hepatic cancer, are estimated to be 1,200,000, 220,000, and 20,000, respectively. A liver disease in some patients is known to proceed into cirrhotic liver in a long period of time, and, among them, some further proceeds into hepatic cancer (A report by the research group on liver diseases, Health and Welfare Ministry, 1979). Prevention, observation, and cure of hepatitis are therefore very important from the aspect of preventing cirrhotic liver and hepatic cancer. In recent years, animal models of hepatitis and hepatic cancers have been developed and their application to the research of liver diseases is ongoing [Mori, M., et al., "Hepatic, Cholecyst, Pancresto", 19. (5), 905–910 (1989)]. Taking rest and diet are principally major means of curing acute hepatitis, while various measures are taken for the cure of active-type chronic hepatitis, especially B-type hepatitis [Kamata, T., "General Clinics", 139 (7), 183–1842 (1990)]. Interferon, adenine arabinoside (Ara-A), and acyclovir (ACV) are named as anti-virus agents used for the cure of hepatitis. Their efficacy is expressed by a seroconversion rate (SC rate: a percentage of patients in which the amount of antigen is converted into negative and the amount of antibody is converted into positive). In the case of interferon, the rate of the seroconversion is 20–30% [Hoofnagle, J. H., et al., Gastroenterol 95, 1318–1325 (1988)], of Ara-A is 0–30% [Garcia, G., et al., Ann. Intern. Med., 107, 278–285 (1987)], and of acyclovir is about 27% [Graeme, J. M., et al., J. Med. Virol., 21, 81–87 (1987)]. Steroid, interferon-gamma, interleukin-2 [IL-2; Kakumau, S., et al., Hepatolgy, 8, 487–492 (1988)], OK423, cianidanole [Blum, A. L., et al., Lancet, 11, 1153–1155 (1977)], levamisole [Fattovich G., et al., Gastroenterology, 91, 692–696 (1986)], and the like are named as immunomodulator. Their efficacy is in the range of 6–30%. The efficacy of the steroid therapy which is considered to be most effective today is 15–45%. However, there are strict limitations imposed to the application of the steroid therapy, requiring selections of a sufficient number of cases concerning the prevention of hepatic disease [Hoofnagle, J. H., et al., Ann. Intern. Med., 104, 12–17 (1986)].

A prolonged use of interferon is reported to involve production of antibodies, imposing a certain limitation to its application to the therapy of hepatitis [Porres, J. C., et al., J. Hepatol., 8, 351–357 (1989)].

Development of a drug which is safe and effective for the therapy of liver diseases are therefore strongly desired.

In view of this situation, the present inventors have undertaken extensive studies for the purpose of developing a drug for the prevention and cure of liver diseases meeting the above requirements. In the course of the studies, the present inventors found that interleukin-1 (hereinafter abbreviated as IL-1) and its derivatives, of which various bioactivities, including the lymphocyte activation activities and promotion of IL-2 or antibody production, had been elucidated and on which a number of researches concerning the application as a drug utilizing its bioactivity had been on going, as well as derivatives of IL-1 which had been developed by the present inventors for the first time, surprisingly possessed an activity of remarkably suppressing the development of liver diseases (liver disease inhibitive activity) and was effective as a drug for preventing and curing liver diseases satisfying the above purposes. The present invention was completed based on this finding.

DISCLOSURE OF THE INVENTION

The present invention relates to a drug for the prevention or cure of liver diseases comprising at least one compound selected from IL-1 and its derivatives as an effective component.

The drug for the prevention or cure of liver diseases of the present invention, as mentioned above, comprises as its essential component IL-1 or its derivative, exhibits a remarkable liver disease inhibitive activity based on this effective component, and is thus very effective for the prevention or cure of liver diseases.

BRIEF DESCRIPTION OF THE DRAWINGS

FIG. 1 is a graph showing the changes in the GPT activity as a result of pharmacological tests conducted on LEC hepatitis model rats according to Example 2.

FIG. 2 is a graph showing the changes in the glutamic-oxaloacetic transaminos (GOT) activity as a result of pharmacological tests conducted on LEC hepatitis model rats according to Example 2.

BEST MODE FOR CARRYING OUT THE INVENTION

Figure 3:
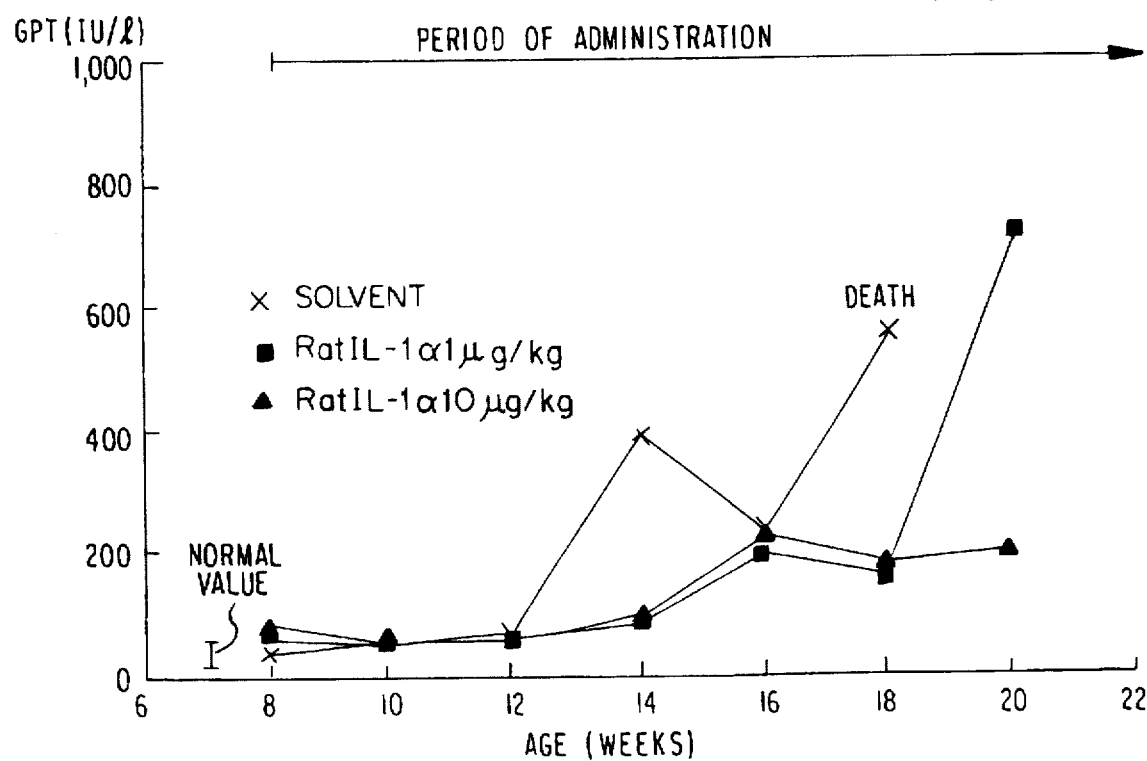
FIG. 3 is a graph showing the changes in the GPT activity as a result of pharmacological tests conducted on LEC hepatitis model rats according to Example 3.

IL-1 which is an effective component of the curing drug of the present invention includes both IL-1α and IL-1β which possess a 159 amino acid sequence and 153 amino acid sequence, respectively, identified based on the nucleotide sequence of a gene encoding a polypeptide exhibiting the LAF (lymphocyte activation factor) activity [Proc. Natl. Acad. Sci., 81, 7907–7911 (1984); Nature, 315, 641 (1985); Nucleic Acid Research, 13 (16), 5869 (1985)]. They may be either natural types which are extracted and isolated from cells in which they are produced by a conventional method, or recombinant types which are obtained by a gene manipulation technique.

Various types of IL-1 derivatives are included; typical examples are IL-1α derivatives and IL-1β derivatives possessing various types of amino acid sequences, on which applications for patent was previously filed [see European Patent publication No. 187991, Japanese Patent Laid-open (ko-kai) No. 152398/1988 (European Patent Publication No. 237967), Japanese Patent Laid-open (ko-kai) No. 164899/1988 (European Patent Publication No. 237073), Japanese Patent Laid-open (ko-kai) No. 167298/1990 (European Patent Publication No. 352816), etc.].

Following compounds are given as examples of the above IL-1 derivatives.

(1) A derivative having a modified IL-1α amino acid sequence of SEQ ID No. 1, wherein the modification is that at least one amino acid residue of 36th Asn and 141st Cys is lost or substituted by other amino acid.

(2) A derivative having a modified IL-1α amino acid sequence of SEQ ID No. 2 (wherein each Xaa represents an α-amino acid residue constituting a human body), wherein the modification is at least one of the followings: 16th Arg is lost, 16th Arg is substituted by other amino acid, an amino acid sequence from 1st Ser to 14th Phe is lost, and an amino acid sequence from 1st Ser to 15th Met is lost.

(3) A derivative having a modified IL-1α amino acid sequence of SEQ ID No. 3, wherein the modification is at least one of the following (a)–(d):

(a) at least one of amino acids selected from 1st Ala, 3rd Val, 4th Arg, 5th Ser, 8th Cys, 11th Arg, 30th His, 71st Cys, 93rd Lys, 97th Lys, 98th Arg, 99th Phe, 103rd Lys, 120th Trp, 121st Tyr, and 153rd Ser is lost or substituted by other amino acid residues.

(b) An amino acid sequence from the 1st Arg to 9th Thr or at least one amino acid residue among the amino acid sequence is lost; excluding the case where at least one of amino acid residues selected from the group consisting of 1st Ala, 3rd Val, 4th Arg, 5th Ser, and 8th Cys as defined in (a) above is lost.

(c) An amino acid sequence from the 103rd Lys to 153rd Ser or at least one amino acid residue within the amino acid sequence is lost; excluding the case where at least one of amino acid residues selected from the group consisting of 103rd Lys, 120th Trp, 121st Tyr, and 153rd Ser as defined in (a) above is lost.

(d) An amino acid residue or an amino acid sequence from 1'st Met to 116'th Asp of SEQ ID No. 4 or a portion of the amino acid sequence on the C-terminal side thereof is added to the N-terminal of SEQ ID No. 3.

Descriptions of above formulas, and of amino acids and polypeptides in the present specification are in accordance with the abbreviations in the nomenclature or rules of IUPAC and IUPAC-IUB, and with the abbreviations commonly used in the art. Numbers and sites of amino acid residues are expressed in accordance with the amino acid sequences of SEQ ID No. 1 (in the case of IL-1α) and SEQ ID No. 3 (in the case of IL-1β), even if there are lost or added amino acid residues; provided that a designation of an amino acid residue site with a dash (') in IL-1β derivatives is in accord with SEQ ID No. 4.

Each of the above IL-1 derivatives includes polypeptides having amino acid sequences of IL-1α and IL-1β in which a specific amino acid residue at a specific site is substituted by other amino acid residue or in which an amino acid residue is added to a specific site. The amino acid residues to be replaced or added may be any α-amino acid residues constituting a human body, with neutral amino acid residues being especially preferable; provided that taking it into consideration that Cys may form an intramolecular disulfide bond due to its SH group, the amino acid residue is preferably other than Cys.

In the case of IL-1α derivatives, given as examples of especially preferable α-amino acid residues constituting a human body are Gly for 16th Arg, Asp for 36th Ash, and Ser for 141st Cys.

For IL-1β derivatives in the same way, examples given of especially preferable α-amino acid residues are Gly, Lys, Gln, or Asp for 4th Arg, Ser or Ala for 8th Cys, Gln for 11th Arg, Tyr for 30th His, Ser, Ala, or Val for 71st Cys, Leu or Asp for 93rd Lys, Leu for 98th Arg, Gln for 103rd Lys, Arg for 120th Trp, Gln for 121st Tyr, and Met, Leu, Arg, or Asp for the addition to the N-terminal.

IL-1α, IL-1β, and their derivatives have conventionally been known to possess the LAF activity, the growth inhibiting activity of tumor cell (GIF activity), activities promoting production of various cytokines, e.g., colony stimulating factors (CSF), interferon (IFN), IL-2, interleukin-3 (IL-3), etc.; antiphlogistic activity, radio-protective activity and the like. They are known to be useful as drugs such as, for example, immune-stimulants, e.g., antibody production promoters, vaccine promoters, etc., antitumor agents, cytokine (e.g., CSF, IL-2, IL-3, etc.) production promoters, antiphlogistics, agents for preventing radiation disorders, and the like. IL-1, however, has not been known to exhibit the effects of preventing or curing liver diseases; there has been no report on the relationship between the effects of preventing or curing liver diseases and the above-mentioned various pharmacological effects. The effects of IL-1s on the prevention and cure of liver diseases are discovered for the first time by the present inventors.

Various derivatives of IL-1α or IL-1β which are active components in the curing agent of the present invention are known compounds or can be prepared by known gene manipulation techniques. Specifically, a desired derivative can be prepared by utilizing a gene encoding the above-mentioned specific polypeptide, recombining it into a vector of a microorganism, and effecting replication, transcription, and translation within cells of the microorganism. This method is more advantageous especially because of its adaptability to massproduction.

A gene used in the above method can be totally synthesized according to a conventional method, e.g., the phosphite triester method [Nature, 310, 105 (1984)] by the chemical synthesis of nucleic acid, or more conveniently, may be synthesized by the utilization of a gene encoding IL-1 or its precursor. For example, it can easily be prepared by using such a gene as a raw material and by its modification into a nucleic acid sequence encoding said specific amino acid sequence according to a conventional method, including said chemical synthesis. Known genes can be used as a raw material gene encoding IL-1 or its precursor (see e.g., Japanese Patent Laid-open (ko-kai) No. 174022/1987).

A method known in the art can also be applicable to the procedures for the modification of nucleic acid (nucleotide) sequence. Such a method can be applied depending on the amino acid sequence of the target polypeptide [see, e.g., Molecular Cloning, Cold Spring Harbor Laboratory (1982) for gene manipulation techniques].

For example, common enzymatic treatment methods are applicable to the DNA digestion, ligation, phosphorylation, etc., by using various enzymes, such as restriction endonuclease, DNA ligase, polynucleotide kinase, DNA polymerase, and the like. These enzymes are readily available as commercial products. Conventional methods, e.g., the agarose gel electrophoresis, may also be followed for the isolation or purification of genes or nucleic acids in these procedures. A method utilizing common vectors, some of which are later mentioned, can be applied to the replication of genes thus obtained. DNA fragments encoding a desired amino acid sequence and synthetic linkers can easily be prepared by the above-mentioned chemical synthesis.

Codons corresponding to such a desired amino acid sequence are known per se in the art, and they can be arbitrarily selected; conventional methods may be followed by taking into consideration the factors such as, for example, the codon utilization frequency by the host and the like [see Nucl. Acids. Res., 4, 43–74 (1981)]. Furthermore, for the partial modification of codons in these nucleic acid sequences a method, for example, such as the site-specific mutagenesis [Proc. Natl. Acad. Sci., 81, 5662–5666 (1984)] in which primers consisting of synthetic oligonucleotides of approximately 15–30 mers encoding the desired modification are used, or the like is used according to a conventional manner.

Determination and confirmation of the nucleotide sequence of the desired gene obtained by the above-mentioned methods can be made, for example, by the Maxam-Gilbert chemical modification method [Maxam, A. M. and Gilbert, W., Meth. Enzym., 65, 499–560 (1980)], the dideoxynucleotide chain termination method in which M13 phage is used [Messing, J. and Vieira, J., Gene., 19, 269–276 (1982)], or the like.

Specific embodiments of the aforementioned procedures and methods are partly shown in Reference Examples hereinafter. The methods, however, are not restricted to them, but any of the various methods commonly known in the art can be applicable.

Genes encoding polypeptides possessing above-mentioned specific amino acid sequences are thus provided (such genes are hereinafter called "target genes").

The above-mentioned specific polypeptide can be prepared according to general gene recombinant techniques known in the art by the utilization of the above-mentioned target gene. Specifically, a recombinant DNA enabling host cells to express the above-mentioned target gene is prepared and inserted into the host cells to transform the same, followed by cultivation of the transformant.

Either cells from eucaryotes or procaryotes can be used for host cells; the cells from eucaryotes include cells of vertebrates, yeasts, and the like; and cells of vertebrates popularly used are, for example, COS cells which are monkey cells [Gluzman, Y., Cell, 23, 175–182 (1981)], the dihydrofolic acid reductase defective strain from ovarian cells of Chinese hamster (Urlauband, G., Chasin, L. A., Proc. Natl. Acad. Sci., U.S.A., 77, 4216–4220 (1980), and the like, but not limited to these. Expression vectors of vertebrate cells which can be used are those having a promoter in the upstream of the gene which is to be expressed, an RNA splice site, a polyadenylation site, and a translation termination sequence. In addition, if required, the vectors may contain the a replication source. Included in examples of such expression vectors are pSV2dhfr holding SV40 early promoter aaa [Subramani, S., Mulligan, R., and Berg, P., Mol. Cell. Biol., 1, (9) 854–864 (1981)], and the like, but not limited to these.

As eucaryotes, yeasts are popular. Among yeasts, those belonging to genus Saccharomyces are used with advantage. Named as eucaryote expression vectors for the yeasts which are preferably used are pAM82 holding a promoter for an acidic phosphatase gene [Miyanohara, A., et al., Proc. Natl. Acad. Sci., U.S.A., 80., 1–5 (1983)] and the like.

*Escherichia coli* and *Bacillus subtilis* are popular procaryote host cells. For example, a replicable plasmid vector is used in the host bacterium. Such a plasmid vector may be an expression plasmid vector which is provided with a promoter and SD nucleotide sequence, in the upstream of the gene to be expressed, and ATG necessary for the protein synthesis to be initiated. Among bacteria of *Escherichia coli* used as a host cell, *Escherichia coli* K12 and the like are popularly used, and pBR322 is a popular vector. Host cells and vectors, however, are not limited to these; all various bacteria and vector known in the art are usable. As a promoter, for example, tryptophan promoter, $P_L$ promoter, lac promoter, 1 pp promoter, and the like can be used; all of them are capable of expressing the target gene.

Illustrating the case where a tryptophan promoter is used, vector pTM1 [Imamoto, F., "Taisha (Metabolism)" 22, 289 (1985)] holding a tryptophan promoter and SD sequence is used as an expression vector, and at the restriction endonuclease Cla I site in the downstream of the SD sequence a gene encoding a desired polypeptide, optionally provided with ATG, is linked. The expression is not always limited to the direct expression system; the expression by the fused protein expression system utilizing β-galactosidase, β-lactamase, or the like is applicable.

Conventional methods can be applied to the introduction of the expression vector thus prepared into host cells and the transformation; for example, a method comprising collecting cells mainly under the logarithmic growth phase, treating the cells with $CaCl_2$ so as to make the cells to be readily taken into the vector, and introducing the vector. In this method, as is conventionally known, it is possible for the medium to include $MgCl_2$ or $RbCl$ in order to further promote the efficiency of the transformation. Furthermore, a method wherein the transformation is initiated after the host cells have been modified with spheroplast or protoplast.

The desired transformant thus obtained can be cultivated according to a conventional method, and the desired polypeptide is produced and accummulated by the cultivation. A medium used for the cultivation can be any medium among various media conventionally used for common cell cultivation. Specific examples of such medium are L medium, E medium, M9 medium, and the like, as well as those media to which commonly known various carbon sources, nitrogen sources, inorganic salts, vitamins, and the like are added. When the tryptophan promoter is used, the cultivation can be carried out by using, for example, M9 minimum medium to which casamino acid is added in order to render the promoter to be functional, and at a suitable time in the course of the cultivation a chemical which may strengthen the function of the tryptophan promoter, e.g., indole acrylic acid, etc., can be added to the medium.

Purification and isolation of the target polypeptide, i.e., the above-mentioned specific IL-1 derivative, from the cultivation product containing the active substance can be carried out according to a conventional method. For the extraction of said polypeptide from host cells, use of mild conditions, e.g., the osmotic pressure shock method, etc., is more desirable from the aspect of the prevention of denaturation of proteins.

The purification and isolation can be carried out according to various treatment procedures in which, for example, physical and chemical characteristics of the polypeptide are utilized [see, e.g., "Biochemistry Data Book II", 1175–1259, 1st edition of Jun. 23, 1980, Tokyo Kagaku-Dojin Dojin Publishing Co.]. Specific examples of said methods which can be employed include a conventional protein precipitation treatment, ultrafiltration, molecular sieve chromatography (gel filtration), liquid chromatography, centrifuge, electrophoresis, affinity chromatography, dialysis, and combinations of these.

More specifically, said procedure can be carried out, for example, according to the following manner. Firstly, the target polypeptides from the culture liquid supernatant is partially purified in advance. This partial purification can be carried out by the treatment in which an organic solvent, e.g., acetone, methanol, ethanol, propanol, dimethylformamide (DMF), etc., or an acidic reagent, e.g., acetic acid, perchloric acid (PCA), trichloroacetic acid (TCA), etc., is used as a protein precipitator; a treatment in which a salting agent, e.g., ammonium sulfate, sodium sulfate, sodium phosphate, etc., is used; and/or an ultrafiltration treatment in which a dialysis membrane, a plate membrane, hollow fibers, or the like is used; and the like. These treatments can be carried out according to the same manner and under the same conditions as usually employed in these types of treatments.

Next, the crude product obtained by the above treatments is subjected to gel filtration to collect fractions exhibiting the activity of the target substance. Here, there are no specific restrictions as to the gel filtration agents to be used. All filters using, for example, dextran gel, polyacrylamide gel, agarose gel, polyacrylamide-agarose gel, cellulose, or the like as a material, can be used. Specific examples which can be given are commercial products such as Sephadex G-type, Sephadex LH-type, Sepharose type, Sephacryl type (all products of Pharmacia Co.), Cellulofine (Chisso Corp.), Biogel P-type, Biogel A-type (Biolad Co.), Ultrogel (LKB Co.), TSK G-type (Tosoh Co.), and the like.

The target polypeptide can be further purified by subjecting active fractions obtained by said gel filtration to hydroxyapatite column chromatography, ion-exchange column chromatography, e.g., DEAE, CM, SP, etc., a chromatofocussing method, reversed phase high performance liquid chromatography, or the like, or to a combination of these procedures, thus isolating and collecting the above-mentioned specific polypeptide which is an IL-1α derivative or an IL-1β derivative, as a homogeneous substance.

The drug for the prevention or cure of liver diseases of the present invention has as its essential feature the incorporation of IL-1α, IL-1β, or a derivative of these, as an effective component, with other components being the same as those in common pharmaceutical compositions. Other than these components, a pharmacologically effective component or conventional components may be arbitrarily incorporated. The drug may be prepared into a form of a pharmaceutical composition adaptable to its application according to conventional methods.

Given as examples of other components which can be incorporated into the above-mentioned pharmaceutical compositions are, especially from the aspect of stabilizing the IL-1 active component, albumins, e.g., human serum albumin (HSA), etc., common L-type amino acids, preferably cysteine, glycine, etc. The amounts of these components to be added are not specifically restricted. Suitable amounts are about 0.01–10 mg of albumins and about 0.001–10 mg of amino acids (the total amount of amino acids when two or more of them are added) for 1 µg of IL-1 active compound. Furthermore, incorporated optionally into the above-mentioned pharmaceutical compositions are sugars, such as monosaccharides, e.g., glucose, mannosed galactose, fructose, etc.; sugar alcohols, e.g., mannitol, inositol, xylitol, etc.; disaccharides, e.g., sucrose, maltose, lactose, etc.; and polysaccharides, e.g., dextran, hydroxypropyl starch, etc., preferably, sucrose, maltose, mannitol, inositol, dextran, etc.; ionic or nonionic surface active agents, especially surface active agents such as polyoxyethylene glycol sorbitan alkyl esters, polyoxyethylene alkyl ethers, sobitan monoacyl esters, fatty acid glycerides, and the like. The above sugars are incorporated about 0.1 mg or more, preferably about 1–100 mg, for 1 µg of IL-1 active compound, and the above surface active agents are incorporated about 0.0001 mg or more, preferably about 0.001–0.1 mg, for 1 µg of IL-1 active compound.

Illustrating the method by which the drug of the present invention is prepared, said drug is prepared into a form of a drug composition generally by incorporating a pharmaceutically effective amount of IL-1 active compound (IL-1α, IL-1β, or a derivative of these) and the above-mentioned optional components, along with a suitable pharmaceutical preparation carrier. As the pharmaceutical preparation carrier, any carriers commonly used for the preparation of drugs depending on the use to which they are directed, such as excipients or diluents, e.g., fillers, extenders, binders, wetting agents, disintegrators, etc., can be used. There are no limitations to the form of the drug composition so long as the same effectively contains IL-1 active compound which is the effective component. It may be a solid preparation, e.g., tablet, powder, granule, pill, etc., or an injection, e.g., liquid, suspension, emulsion, etc. Alternatively, it can be prepared into a dry product which can be made liquid by the addition of a suitable carrier. All these drug compositions can be prepared by conventional methods.

There are no special limitations as to the buffer solutions which can be used as a carrier for the above compositions; buffer solutions such as citric acid-sodium phosphate, citric acid-sodium citrate, acetic acid-sodium acetate, disodium phosphate-phosphoric acid-sodium phosphate, citric acid-siliceous sand, and the like, of which the pH is 4–8, and preferably 5–6, are given as preferable examples.

Drug compositions thus prepared can be administered through a suitable dosing route depending on their form; for example, injection preparations are administered by intravenous, intramuscular, hypodermic, intracutaneous, or intraperitoneal injection, and solid preparations are orally or enterally dosed. Amounts of effective components in the drug composition and a dose of the composition to be administered are not fixed but suitably determined depending on the manner by which they are administered, the form of the composition, the purpose for which the drug is used, symptoms of the patient to whom the drug is administered, and the like. Usually, the drug is prepared into a composition containing about 0.00001–80wt. % of the effective components, and desirably dosed in an amount such that the effective components contained therein be in the range of about 0.01 µg to 10 mg per day per adult. The administration need not be one time per day; the drug may be dividedly dosed 3–4 times a day.

EXAMPLES

The present invention is hereinafter illustrated in more detail by way of examples and reference examples. In examples below biological activities are measured according to the following methods.

[Measurement of Activities]

(1) Measurement of IL-1 activity

The activity was indicated by the LAF activity measured on C3H/He J-series mouse thymocytes according to the method of Oppenheim [Oppenheim, J. J., et al., J. Immunol., 116, 1466 (1976)].

(2) Measurement of GIF activity 0.1 ml of sample solutions with various concentrations were placed in a 96-well microplate (Corning Co.). Then, 0.1 ml of Eagle's MEM suspension containing 10% FCS which contains human melanoma cell A375 at a concentration of 2×10⁴/ml was added to each well, and cultivated for 4 days in a $CO_2$ gas cultivator (a product of Narco Co.). After the cultivation, 0.05 ml of neutral red (a product of Wako Pure Chemical Co.) was added to each well and the cultivation was continued for 2 hours at 37° C. After removal of the supernatant, 0.3 ml of a phosphate buffer-physiological saline was gently added to each well to wash it. After removal of the washing liquid, 0.1 ml of a 1:1 mixture of monosodium phosphate-ethanol was added to each well, and the plate was shaken for several minutes in a micromixer. The amount of pigment taken into cells was measured by a 96-well microtitration plate photometer (Titer check multiscan; a product of Flow laboratories Co.) at the absorbance of 540 nm to determine the proliferation inhibitory activity. The reciprocal of the dilution factor of sample groups inhibiting 50% of the cell proliferation of the control group, i.e., the groups exhibiting one half of the absorbance of the control group, was taken as one unit of the GIF activity. This means that if a sample solution has 10 unit of GIF activity, for example, the solution, when diluted to 10-fold, still exhibits an activity of inhibiting 50% of the cell proliferation.

Reference Example 1

Preparation of In-1α derivative (16G•36D•141S)

(1) Preparation of plasmid for expressing IL-1α derivative

Plasmid p trp IL-1α-141S used in this example was, as described in European Patent Publication No. 237073, has been prepared by utilizing plasmid pcD-GIF-207 [a plasmid held by *Escherichia coli* χ1776/pcD-GIF-207 (FERM 1294)] having a cDNA encoding an IL-1α precursor protein and pTM1 [Imamoto, F., "Taisha (Metabolism)" 22, 289 (1985)] by the site-specific mutagenesis [Proc. Natl. Acad. Sci., 81, 5662–5666 (1984)]. This plasmid holds a gene encoding an IL-1α derivative with an amino acid sequence of SEQ ID No. 1 of which 141st Cys has been substituted by Ser.

A Cla I-Bam HI DNA fragment (527 bp) was cut out from the above plasmid p trp IL-1α-141S, and ligated with a Cla I-Bam HI long-chain fragment of vector f1•IL-1β 1 ppT [Biochem. Biophys. Res. Commun., 150, 1106–1114 (1988)] for the IL-1β site-specific mutagenesis to produce f1•IL-1α-141S. Helper phage M13KO7 (Takarashuzo) was infected with it to obtain a single stranded DNA (ssDNA), which was served as a mold for the mutagenesis.

The site-specific mutagenesis was carried out by using 5'-phosphorylated synthetic oligonucleotide SEQ ID No: 5 (5'-ACTTTATGGGGATCATCA-3') which was phosphorylated with T4 polynucleotide kinase, as a primer, by an oligonucleotide-directed in vitro mutagenesis (a product of Amersham Co, UK).

An ssDNA was obtained from a clone which had been transformed into *E. coli* MV1304 (Takarashuzo), and DNA sequencing was performed by the dideoxy chain termination method to obtain a recombinant (transformant) f1•IL-1α-16G•141S/*E. coli* MV1304, of which the target gene was mutated.

This plasmid is a plasmid for the expression of a polypeptide with an amino acid sequence of SEQ ID No. 1 of which 16th Arg was substituted by Gly, 36th by Asn, and 141st Cys by Ser.

This transformant has been deposited with Fermentation Research Institute, Agency of Industrial Science and Technology, as *Escherichia coli* MV 1304/f1•IL-1α•16G•141S (FERM BP-2434).

(2) Cultivation of the Transformant

The transformant (MV1304/f1•IL-1α-16G•141S) obtained in (1) above was inoculated into 600 ml of LB medium with the following composition and containing 100 µg/ml of ampicillin. The mixture was shaken at 37° C. overnight to obtain the above-mentioned culture liquid.

| (LB medium composition) | |
|---|---|
| Bacto-tryptone (Difco Co.) | 10 g/l |
| Bacto yeast extract (Difco Co.) | 5 g/l |
| NaCl (Wako Pure Chemical Co.) | 10 g/l |

600 ml of the above culture liquid was inoculated into 30 l of a culture medium with the following composition, and cultivated in a 50 l jar fermenter (Hitachi Ltd.) at 36.5° C. for 14 hours under the conditions of 0.5 VVM (aeration) and 120 rpm (rotation).

| (Culture medium composition) | |
|---|---|
| $Na_2HPO_4.12H_2O$ | 6 g/l |
| $KH_2PO_4$ | 3 g/l |
| NaCl | 0.5 g/l |
| $NH_4Cl$ | 1 g/l |
| Bacto-casamino acid | 10 g/l |
| Bacto-yeast extract | 0.5 g/l |
| L-cysteine.HCl | 75 mg/l |
| L-proline | 75 mg/l |
| L-leucine | 75 mg/l |

After adjusting the pH to 7.4 with 4N NaOH, the mixture was treated in an autoclave at 121° C. for 30 minutes or heated with steam at 123° C. for 20 minutes, followed by the addition of a separately sterilized liquid with the following composition in a sterilized manner.

| (Separately sterilized liquid composition) | |
|---|---|
| 1 M $MgSO_4.4H_2O$ | 2 ml/l |
| 1 M $CaCl_2.2H_2O$ | 0.1 ml/l |
| 7.5 mg/l thiamine.HCl | 1 ml/l |
| 40% glucose | 18.75 ml/l |

After the cultivation, *E. coli* was suspended into 300 ml of 1M $Na_2HPO_4$ and allowed to stand in a cold room overnight. Next, the suspension was dialyzed in the cold room against 10 mM Tris-HCl buffer solution (pH 8.0) for 2 days and the dialyzing fluid obtained was centrifuged (16,000×g) to separate the supernatant from the precipitate.

(3) Purification of IL-1α Derivative

The supernatant obtained in (2) above was adjusted to pH 3 with 2M acetic acid and purified by SP-HPLC [a product of Tosoh Co., TSK gel SP-5PW column (5.5×20 cm) was used] under the following conditions.

Column: TSK gel SP-5PW (5.5×20 cm, manufactured by Tosoh Co.)

Eluent A: 50 mM sodium acetate (pH 4.5)

Eluent B: 50 mM sodium acetate (pH 5.5)

| Concentration gradient: Time (minutes) | % B |
|---|---|
| 0 | 0 |
| 30 | 0 |
| 130 | 100 |
| 160 | 100 |

-continued

| Concentration gradient: Time (minutes) | % B |
|---|---|
| 165 | 0 |
| 195 | 0 |

Flow rate: 30 ml/min

As a result of the above treatment, the GIF active fractions were recognized in 114–131 retention time.

Next, the active fractions obtained by the above treatment was again subjected to the SP-HPLC under the same conditions to obtain GIF active fractions.

The active fractions thus obtained were collected and purified by ion-exchange chromatography (DEAE-HPLC).

Column: TSK gel DEAE-5PW (5.5×20 cm, manufactured by Tosoh Co.)

Eluent A: 20 mM Tris-HCl buffer solution (pH 8.0)

Eluent B: 20 mM Tris-HCl buffer solution (pH 8.0) containing 0.5M NaCl.

| Concentration gradient: Time (minutes) | % B |
|---|---|
| 0 | 0 |
| 30 | 0 |
| 150 | 60 |
| 155 | 100 |
| 185 | 100 |
| 190 | 0 |

Flow rate: 30 ml/min

As a result of the above treatment, the GIF active fractions were recognized in 98.8–102.8 retention time.

Active fractions obtained by the above treatment were collected and concentrated by ultrafiltration (YM-5 membrane, a product of Amicon Co. was used) while replacing the buffer solution so as to make the solution composition 20 mM sodium phosphate buffer solution (pH 7.0) to obtain a concentrated pure product.

The product had an isoelectric point of 5.0.

(4) Confirmation of IL-1α Derivative (i) Amino acid composition

30 µl of the concentrated pure product obtained in (3) above was placed with care in the bottom of a 6 mm×50 mm hard test tube with a thick wall. The test tube was placed in a reaction vial to dry it under reduced pressure by the picotag work station (manufactured by Waters Co.). 200 µl of 6N hydrochloric acid (containing 1% phenol) was added to the test tube and deaeration was performed with care, following which the tube was sealed and hydrolysis was carried out at 130° C. for 4 hours.

After the hydrolysis, 400 µl of 0.02N hydrochloric acid was added and the mixture was served as a sample for the amino acid analysis.

The amino acid analysis was carried out on 250 µl of the above sample by an amino acid analyzer (Hitachi 835 Type Analyzer, manufactured by Hitachi Ltd.). Separated amino acids were analyzed by the orthophthal aldehyde method. The quantitative analysis was carried out by using a calibration curve prepared by the analyses on standard amino acids conducted prior to and after the analysis.

The results, the mol ratio of each amino acid taking Phe as a standard (10 mol), are shown in Table 1. Pro, Cys and Trp could not be analyzed under the above conditions of analysis.

TABLE 1

| Amino acid | mole ratio |
|---|---|
| Asp and/or Asn | 21.1 |
| Thr | 11.2 |
| Ser | 11.5 |
| Glu and/or Gln | 18.3 |
| Gly | 8.8 |
| Ala | 14.3 |
| Val | 6.8 |
| Met | 2.0 |
| Ile | 10.4 |
| Leu | 15.2 |
| Tyr | 6.7 |
| Phe | (10) |
| Lys | 11.1 |
| His | 3.2 |
| Arg | 2.7 |

(ii) Amino acid sequence

50 µl (corresponding to 298 pmol) of the concentrated pure product obtained in (3) above was analyzed by the protein sequencer (Model 470A) made by Applied Biosystem Co. The produced PTH-amino acid was appropriately diluted with 100–500 µl of 33% aqueous solution of acetonitrile, 5 µl of which was charged into the Waters 710 B-type auto-sampler. Two Beckman 112-type pumps were operated on 421-type controller in the chromatography system. A 2 mm×250 mm column filled with ultrasphere ODS-5 µm was used and maintained at 55° C. by a column heater. The separation was performed by the gradient elution method by using a mixed solution of 20 mM sodium acetate-acetonitrile mixture at a flow rate of 0.3 ml per minute, and monitored at 269 nm. The time required for the analysis was 45 minutes.

As a result, the amino acid sequence on the N-terminal region was identified as SEQ ID No: 6, which is as follows.

Ser Ala Pro Phe Ser Phe Leu Ser Asn Val Lys Tyr Asn Phe Met Gly
              5                    10                 15

Ile Ile Lys Tyr Glu Phe Ile Leu Asn Asp Ala Leu Asn Gln Ser Ile
         20                  25                 30

Ile Arg Ala Asp
   35

Based on the above results, the purified product was confirmed to be a polypeptide having an amino acid sequence of In-1α derivative represented by SEQ ID No. 2 of which the 16th amino acid (Arg) was substituted by Gly. In the gene, the 36th amino acid was Asn, while the pure product obtained had Asp for the 36th amino acid. The fact demonstrates that, as is observed in the natural type IL-1α, a derivative with Asp at the 36th amino acid is stable, and that the same type of mutation has occurred in the IL-1α derivative of this example.

Reference Example 2

Preparation of IL-1α derivative (Delta(1-14)•36D•141S)

(1) Preparation of plasmid for expressing IL-1α derivative

The experiment was performed on plasmid p trp IL-1α-36D•141S [described in European Patent Publication No. 237073, *Escherichia coli* HB101 holding this plasmid is deposited with Fermentation Research Institute, Agency of Industrial Science and Technology in the name of *Escherichia coli* HB101/IL-1α-36D•141S (FERM BP-1295)] according to the site-specific mutagenesis as follows.

A Cla I-Bam HI DNA fragment (527 bp) was cut out from the above plasmid p trp IL-1α-36D•141S, and ligated with the same Cla I-Bam HI long-chain fragment of vector f1•IL-1β 1 ppT as used in Reference Example 1 to produce f1-IL-1α-36D•141S. Helper phage M13K07 (Takarashuzo) was infected with it to obtain a single stranded DNA, which was served as a mold for the mutagenesis.

The site-specific mutagenesis was carried out by using synthetic oligonucleotide SEQ ID No: 7 (5'-AAGGGTATCGATTATGATGAGGATCATC-3') as a primer by the oligonucleotide-directed in vitro mutagenesis in the same manner as in Reference Example 1.

An ssDNA was obtained from a clone which had been transformed into E. coli MV1184 (Takarashuzo) and DNA sequencing was performed by the dideoxy chain termination method to obtain a recombinant (transformant) f1•IL-1α-Delta(1-14)36D•141S/E. coli MV1184, of which the target gene was mutated.

This plasmid is a plasmid for the expression of a polypeptide with an amino acid sequence of SEQ ID No. 2 from which the 1–14 amino acid sequence was lost and of which 36th Xaa was substituted by Asp and 141st Xaa by Ser.

This transformant has been deposited with Fermentation Research Institute, Agency of Industrial Science and Technology, as *Escherichia coli* MV 1184/f1•IL-1α-Delta(1-14)36D-141S (FERM BP-2433).

Expression and purification of the target IL-1α derivative was carried out in almost the same way as in Reference Example 1.

In this manner the target derivative, IL-1α-Delta(1-36D-141S, was obtained.

Its specific activity was $1.0 \times 10^6$ GIF unit/mg of protein.

(2) Confirmation of IL-1 Derivative (i) Amino acid composition

The amino acid composition of the IL-1α derivative obtained in (1) above was carried out in the same manner as Reference Example 1, (4), (i).

The results obtained as Phe=7 are shown in Table 2.

TABLE 2

| Amino acid | mole ratio |
|---|---|
| Asp | 19.0 |
| Thr | 11.0 |
| Ser | 7.1 |
| Glu | 16.3 |
| Gly | 5.3 |
| Ala | 13.2 |
| Val | 5.8 |
| Met | 4.0 |
| Ile | 10.3 |
| Leu | 13.8 |
| Tyr | 5.7 |
| Phe | (7) |
| Lys | 10.0 |
| His | 3.2 |

(ii) Amino acid sequence

The amino acid sequence on the N-terminal region of the In-1α derivative obtained in (1) above was carried out in the same manner as Reference Example 1, (4), (ii).

As a result, the amino acid sequence of 15 amino acids on the N-terminal was found to be represented by SEQ ID No: 8 as follows.

Met Met Arg Ile Ile Lys Tyr Glu Phe Ile Leu Asn Asp Ala Leu
                5               10              15

Based on the above results, the derivative obtained was confirmed to have an amino acid sequence of IL-1α represented by SEQ ID No. 2, but devoid of the 1-14 amino acid sequence.

Reference Example 3

Preparation of IL-1α derivative [Delta(1-15)]

(1) Preparation of plasmid for expressing IL-1derivative

Vector f1•IL-1β 1 ppT [Biochem. Biophys. Res. Commun., 150, 1106–1114 (1988)] for the IL-1β site-specific mutagenesis was used in this example. First, the vector f1•IL-1β 1 ppT was digested with Eco RI, treated with DNA polymerase I (Klenow fragment), and self-ligated to prepare f1•-IL-1β 1 ppT DeltaRI, from which the Eco RI site was lost. An Hpa I-BamHI long-chain fragment was cut out from this plasmid.

Separately, Eco RI-Bam HI short-chain fragment was cut out from plasmid p trp IL-1α-113 [described in European Patent Publication No. 237073] and combined with the above Hpa I-BamHI long-chain fragment with a synthetic linker (5'-AACTAGTACGCAAGTTCACGTAA-GGAGGTTTAATATTATGAGAATCATCAAATACG-3' (SEQ ID No: 9) and 5'-AATTCGTATTTGATGATTCTCAT-AATATTAAACCTCCTTACGTGAACTTGCGTACTAG-TT-3' SEQ ID No: 10) to obtain a recombinant (transformant) f1•IL-1α-Delta(1-15)/E. coli MV1184, of which the target gene was mutated.

This plasmid is a plasmid for the expression of a polypeptide with an amino acid sequence of SEQ ID No. 2 from which the 1-15 amino acid sequence was lost and of which 36th Xaa was substituted by Asn and 141st Xaa by Cys.

(2) Preparation of IL-1derivative

The expression and purification of the target IL-1α derivative was performed by using the above plasmid and according almost to Reference Example 1.

Specifically, *E. coli* HB101 holding the above plasmid f1•IL-1α•Delta(1-15) was cultivated in the same manner as in Example 1 (60 l) and cells were collected by centrifugation (16,000×g). The cells were suspended into 1M phosphate buffer solution (pH 6.0), left in a cold room overnight, and dialyzed against 0.1M phosphate buffer solution (pH 6.0) for 2 days and the dialyzing fluid obtained was centrifuged (16,000×g), to separate the supernatant from the precipitate. The same procedure was further repeated twice on the precipitate obtained, collecting each time the supernatants. The supernatants were combined and subjected to the following purification.

(3) Purification of IL-1α Derivative

The supernatant obtained in (2) above was purified by DEAE-HPLC [a product of Tosoh Co., TSK gel DEAE-5PW column (5.5×20 cm) was used] under the following conditions. Column: TSK gel DEAE-5PW (5.5×20 cm, manufactured by Tosoh Co.)

Eluent A: 20 mM Tris-HCl (pH 8.0)

Eluent B: 20 mM Tris-HCl (pH 8.0)+0.5M NaCl

| Concentration gradient: Time (minutes) | % B |
|---|---|
| 0 | 0 |
| 30 | 0 |
| 150 | 60 |
| 155 | 100 |
| 185 | 100 |
| 190 | 0 |

Flow rate: 30 ml/min

Fractions obtained in retention time 88–93 minutes (Fraction A) and 99–103 minutes (Fraction B) were collected and each fraction was concentrated by ultrafiltration (YM-5 membrane was used) and purified by gel filtration HPLC [TSK gel G-2000 SWG column (21.5×600 mm) manufactured by Tosoh Co. was used; eluent: PBS⁻].

Fraction A purified as above was adjusted to pH 4 with 2M acetic acid and subjected to TSK gel SP-5PW (21.5×150 cm, manufactured by Tosoh Co.). The elution was made under the following conditions.

Eluent A: 50 mM sodium acetate (pH 5.0)

Eluent B: 50 mM sodium acetate (pH 5.0)+0.5M NaCl.

| Concentration gradient: Time (minutes) | % B |
|---|---|
| 0 | 0 |
| 20 | 0 |
| 110 | 45 |
| 115 | 100 |
| 130 | 100 |
| 135 | 0 |

Flow rate: 30 ml/min

Fractions in the retention time of 87-93 minutes were collected and concentrated by ultrafiltration (YM-5 membrane) while replacing the buffer solution so as to make the solution composition 20 mM sodium phosphate buffer solution (pH 6.0) to obtain a concentrated pure product.

(4) Confirmation of IL-1α Derivative (i) The amino acid analysis of purified IL-1α derivative obtained in (3) above was carried out in the same manner as Reference Example 1-(4)-(i).

The results obtained by taking Phe=7 are shown in Table

TABLE 3

| Amino acid | mole ratio |
|---|---|
| Asp | 18.0 |
| Thr | 11.2 |
| Ser | 6.8 |
| Glu | 17.1 |
| Gly | 5.8 |
| Ala | 13.1 |
| Val | 5.7 |
| Met | 2.8 |
| Ile | 10.9 |
| Leu | 14.1 |
| Tyr | 5.9 |
| Phe | (7) |
| Lys | 10.2 |
| His | 3.0 |
| Arg | 3.1 |

(ii) The amino acid sequence on the N-terminal region of the IL-1α derivative obtained in (3) above was analyzed in the same manner as Reference Example 1, (4), (ii) to find the amino acid sequence of 23 amino acids on the N-terminal as follows represented by SEQ ID No: 11.

Met Arg Ile Ile Lys Tyr Glu Phe Ile Leu Asn Asp Ala Leu Asn Gln
              5                          10                15

Ser Ile Ile Arg Ala Asn Asp
          20

Based on the above results, the IL-1α derivative obtained was confirmed to have an amino acid sequence of IL-1α of SEQ ID No. 2, but devoid of the 1-15 amino acid sequence and having Asn substituted for the 36th Xaa.

(iii) Fraction B obtained in (3) above was also purified in the same manner as fraction A and the amino acid sequence of the purified product was analyzed in the same manner.

The results obtained by taking Phe=7 are shown in Table 4.

TABLE 4

| Amino acid | mole ratio |
|---|---|
| Asp | 18.3 |
| Thr | 11.3 |
| Ser | 6.7 |
| Glu | 17.2 |
| Gly | 5.7 |
| Ala | 13.2 |
| Val | 5.8 |
| Met | 2.9 |
| Ile | 10.9 |
| Leu | 14.1 |
| Tyr | 5.9 |
| Phe | (7) |
| Lys | 9.9 |
| His | 3.0 |
| Arg | 3.1 |

(iv) The amino acid sequence on the N-terminal region of the above purified products from Fraction B was analyzed in the same manner as Reference Example 1, (4), (ii) to find the amino acid sequence of 23 amino acids on the N-terminal region represented by SEQ ID No: 12 as follows.

Met Arg Ile Ile Lys Tyr Glu Phe Ile Leu Asn Asp Ala Leu Asn Gln
              5                          10                15

Ser Ile Ile Arg Ala Asp Asp
          20

Based on the above results, the IL-1α derivative obtained was confirmed to have an amino acid sequence of IL-1α represented by SEQ ID No. 2, but devoid of the 1-15 amino acid sequence and having Ash substituted for the 36th Xaa.

Reference Example 4

Preparation of IL-1α derivative (Delta(1-15)•36D•141S)

(1) Preparation of plasmid for expressing IL-1α derivative

In this example plasmid p trp IL-1α•36D•141S was used to perform the site-specific mutagenesis according to the following manner. Specifically, a Cla I-Bam HI DNA fragment (527 bp) was cut out from the above plasmid p trp IL-1α•36D•141S, and ligated with the same Cla I-Bam HI long-chain fragment of f1•IL-1β1 ppT as used in Reference Example 1 to produce f1•IL-1α•36D•141S. Helper phage M13KO7 (Takarashuzo) was infected with it to obtain a single stranded DNA (ssDNA), which was served as a template for the mutagenesis.

The site-specific mutagenesis was carried out by using synthetic oligonucleotide SEQ ID No: 13 (5'-GTATCGATAATGAGAATCATC-3') as a primer by an oligonucleotide-directed in vitro mutagenesis kit (a product of Amersham Co, UK) in the same manner as in Reference Example 1.

An ssDNA was obtained from a clone which had been transformed into E. coli MV1184 (Takarashuzo), and DNA sequencing was performed by the dideoxy chain termination method to obtain a recombinant (transformant) f1•IL-1α•Delta(1-15)•36D•141S/E. coli MV1184, of which the target gene was mutated.

Furthermore, an expression vector for the masscultivation was prepared according to the following manner. First, f1•IL-1β 1 pp T was digested by Mlu I and Sal I, treated with DNA polymerase (Klenow fragment), and ligated with T4 DNA ligase to prepare f1•IL-1β1 ppT DeltaMS. This was further treated with Eco RI, DNA polymerase (Klenow fragment), and self-ligated. Next, the Aat II was converted into Bgl II site by the treatment with Aat II, T4 DNA polymerase, and Bgl II linker SEQ ID No: 15 (pGAAGATCTTC). In the same manner Sal I site was converted into Xba I site by the treatment with Sal I, DNA polymerase (Klenow fragment), and Xba I linker SEQ ID No: 16 (pGCTCTAGAGC). From this a Cla I-Bam HI DNA long chain fragment (5.5 kb) was cut out and ligated with the above Cla I-Bam HI DNA fragment (482 bp) from f1•IL-1α•Delta(1-15)•36D•141S to obtain f1•IL-1α•Delta(1-15)•36D•141SA (Aat II→Bgl II, Sal I→Xba I). From this, a 1109 bp Bgl II-Xba I DNA fragment was cut out.

A 2514 bp Bgl II-Xba I long-chain fragment obtained separately from pAT 153 by substituting Cla I site with Bgl II site and Dra I site with Xba I site and digested with Bgl II and Xba I was ligated with the above 1109 bp Bgl II-Xba I fragment to obtain the target recombinant pAT•IL-1α•Delta(1-15)•36D•141S.

This plasmid was a plasmid expressing an IL-1α derivative with an amino acid sequence of SEQ ID No. 2, but does not have the 1-15 amino acid sequence (provided that if the recombinant is cultivated to produce a protein to which Met is added derived from a translation initiation codon, a polypeptide without the 1-14 amino acid sequence is obtained in practice), and has Asp substituted for 36th Xaa and Ser substituted for 141st Xaa.

This transformant was deposited with Fermentation Research Institute, Agency of Industrial Science and Technology, as Escherichia coli HB 101/pAT IL-1α Delta (1-15)36D•141S (FERM BP-2483).

(2) Cultivation of the Transformant

The above transformant was inoculated into 600 ml of LB medium with the following composition and containing 10 μg/ml of tetracycline, and shaken at 37° C. overnight to obtain a pre-culture liquid.

| (LB medium composition) | |
|---|---|
| Bacto-tryptone (Difco Co.) | 10 g/l |
| Bacto-yeast extract (Difco Co.) | 5 g/l |
| NaCl (Wako Pure Chemical Co.) | 10 g/l |

600 ml of the above culture liquid was inoculated into 30 l of a culture medium with the following composition, and cultivated in a 50 l jar fermenter (Hitachi Ltd.) at 36.5° C. for 16 hours under the conditions of 1 VVM (aeration) and 300 rpm (rotation).

| (Culture medium composition) | |
|---|---|
| $Na_2HPO_4.12H_2O$ | 6 g/l |
| $KH_2PO_4$ | 3 g/l |
| NaCl | 0.5 g/l |
| $NH_4Cl$ | 1 g/l |
| Casein acid hydrolyzate (Sigma Co.) | 10 g/l |
| Bacto-yeast extract | 0.5 g/l |
| $MnCl_2.4H_2O$ | 2.5 mg/ml |
| L-Cysteine.HCl | 75 mg/l |
| L-Proline | 75 mg/l |
| L-Leucine | 75 mg/l |

After adjusting the pH to 7.4 with 4N NaOH, the mixture was treated in an autoclave at 121° C. for 30 minutes, followed by the addition of a separately sterilized liquid of the following composition in a sterilizing manner.

| (Separately sterilized liquid composition) | |
|---|---|
| 1 M $MgSO_4.4H_2O$ | 2 ml/l |
| 1 M $CaCl_2.2H_2O$ | 0.1 ml/l |
| 7.5 mg/l thiamine.HCl | 1 ml/l |
| 40% glucose | 18.75 ml/l |

After the cultivation, cells were collected by centrifugation (16,000 g), suspended into 1M phosphate buffer solution (pH 6.0), and allowed to stand in a cold room overnight. The suspension was dialyzed against 10 mM Tris-HCl buffer solution (pH 8.0) for 2 days and the dialyzing fluid obtained was centrifuged (16,000×g) to separate the supernatant from the precipitate. The above procedure was repeated on the precipitate to obtain a supernatant. The supernatants obtained were combined and subjected to the purification procedure.

(3) Purification of IL-1α Derivative

The supernatant obtained in (2) above was adjusted to pH 3 with 2M acetic acid and purified by SP-HPLC [a product of Tosoh Co., TSK gel SP-5PW column (5.5×20 cm) was used] under the following conditions.

Column: TSK gel SP-5PW (5.5×20 cm, manufactured by Tosoh Co.)

Eluent A: 50 mM sodium acetate (pH 5.0)

Eluent B: 50 mM sodium acetate (pH 5.0)+0.5M NaCl

| Concentration gradient: Time (minutes) | % B |
|---|---|
| 0 | 0 |
| 30 | 0 |
| 90 | 30 |
| 95 | 100 |
| 125 | 100 |
| 130 | 0 |

Flow rate: 30 ml/min

Fractions obtained in retention time of 70–75 minutes were collected, adjusted to pH 8.1 with 1M Tris-HCl buffer solution, subjected to DEAE-HPLC [manufactured by Tosoh Co., TSK gel DEAE-5PW column (5.5×20 cm), and eluted under the following conditions.

Column: TSK gel DEAE-5PW (5.5×20 cm, manufactured by Tosoh Co.)

Eluent A: 20 mM Tris-HCl buffer solution (pH 8.0)

Eluent B: 20 mM Tris-HCl buffer solution (pH 8.0)+0.5M NaCl.

| Concentration gradient: Time (minutes) | % B |
|---|---|
| 0 | 0 |
| 20 | 0 |
| 140 | 60 |
| 145 | 100 |
| 165 | 100 |
| 170 | 0 |

Flow rate: 30 ml/min

Fractions obtained in retention time of 92–96 minutes were collected, concentrated by ultrafiltration (YM-5 membrane was used), and purified by gel filtration HPLC [TSK gel G-2000 SWG column (21.5×600 mm) manufactured by Tosoh Co. was used; eluent: $PBS^-$].

The purified fractions obtained as above was adjusted to pH 4 with 2M acetic acid and subjected to SP-HPLC [TSK gel SP-5PW (21.5×150 mm) manufactured by Tosoh Co.]. The elution was made under the following conditions.

Column: TSK gel SP-5PW (21.5×150 cm) manufactured by Tosoh Co.

Eluent A: 50 mM sodium acetate (pH 5.0)

Eluent B: 50 mM sodium acetate (pH 5.0)+0.5M NaCl.

| Concentration gradient: Time (minutes) | % B |
| --- | --- |
| 0 | 0 |
| 20 | 0 |
| 110 | 45 |
| 115 | 100 |
| 130 | 100 |
| 135 | 0 |

Flow rate: 3 ml/min

Fractions in the retention time of 87–90 minutes were collected and concentrated by ultrafiltration (YM-5 membrane) was used, while replacing the buffer solution so as to make the solution composition 20 mM sodium phosphate buffer solution (pH 7.0) to obtain a pure product.

(4) Confirmation of IL-1α Derivative (i) The amino acid composition of the purified product obtained in (3) above was carried out in the same manner as Reference Example 1, (4), (i).

The results obtained by taking Phe=7 are shown in Table 5.

TABLE 5

| Amino acid | mole ratio |
| --- | --- |
| Asp | 18.6 |
| Thr | 11.4 |
| Ser | 7.7 |
| Glu | 17.2 |
| Gly | 5.7 |
| Ala | 13.2 |
| Val | 5.8 |
| Met | 2.8 |
| Ile | 10.9 |
| Leu | 14.1 |
| Tyr | 5.9 |
| Phe | (7) |
| Lys | 9.9 |
| His | 3.0 |
| Arg | 3.1 |

(ii) The amino acid sequence on the N-terminal represented by SEQ ID No: 14 region the IL-1α derivative obtained in (3) above was analyzed in the same manner as Reference Example 1, (4), (ii) to find the amino acid sequence of 15 amino acids on the N-terminal as follows.

Met Arg Ile Ile Lys Tyr Glu Phe Ile Leu Asn Asp Ala Leu Asn
          5                  10              15

Based on the above results, the IL-1α derivative obtained was confirmed to have an amino acid sequence of IL-1α of SEQ ID No. 2, but devoid of the 1–15 amino acid sequence.

Reference Example 5

Preparation of IL-1β derivative (24-153)

(1) Preparation of expression plasmid

Plasmid p trp GIF-α [see European Patent Publication No. 0187991; E. coli transformed with the plasmid has been deposited with Fermentation Research Institute, Agency of Industrial Science and Technology, dated Dec. 12, 1985 under the name of Escherichia coli χ 1776/p trp GIF-α (FERM BP-949)] was used to construct a plasmid for the expression of the target polypeptide according to the following manner.

Specifically, after digesting p trp GIF-α with restriction endonucleases Nde I and Sal I, a 781 bp DNA fragment containing a region encoding the amino acid sequence following 24th amino acid residue of IL-1β was isolated by the agarose gel electrophoresis. This DNA fragment was treated with DNA polymerase (Klenow fragment) to make blunt the restriction endonuclease Nde I and Sal I cleavage sites.

On the other hand, 5' terminals of 5'-CGATAATG-3' and 5'-CATTAT-3' were phosphorylated with T4 polynucleotide kinase and linked with the above DNA fragment of which the terminals were made blunt by using T4 DNA ligase. The DNA was digested with restriction endonucleases Cla I and BamHI and subjected to agarose gel electrophoresis to isolate and purify a 510 bp DNA fragment.

Furthermore, plasmid pTM1 was digested with restriction endonucleases Cla I and Bam HI and subjected to agarose gel electrophoresis to isolate and purify a DNA fragment of about 4.4 kbp containing trp promoter. This DNA fragment and the 510 bp Cla I-Bam HI DNA fragment previously obtained were linked by using T4 DNA ligase and transformed into Escherichia coli HB 101. The target transformant was selected by the restriction endonuclease analysis of the plasmid DNA obtained by the boiling method [Maniatis, T., Fritsch, E. F., and Sambrook, J., Molecular Cloning, 366 (1982), Cold Spring Harbor Laboratory].

(2) Cultivation of the Transformant

The transformant (E. coli HB101/p trp GIF-α-24-153) was cultivated in 10 ml of LB medium (1% tryptone, 0.5% yeast extract, 0.5% NaCl) containing 50 µg/ml ampicillin and 20 µg/ml L-tryptone, while shaking at 37° C. overnight. 1 ml of the culture liquid was inoculated into 50 ml of M9 minimum medium (0.6% Na$_2$HPO$_4$, 0.3% KH$_2$PO$_4$, 0.05% NaCl, 0.1% NH$_4$Cl, 2 mM MgSO$_4$, 0.2% glucose, and 0.1 mM CaCl$_2$) containing 50 µg/ml ampicillin and 1% casamino acid and shake-cultured at 37° C. Cells were collected when the optical density at 550 nm became 1.0 and suspended into 5 ml of 15% sucrose-50 mM Tris-HCl (pH 8.0)-50 mM EDTA (pH 8.0). After the addition of 500 µl of 10 mg/ml lysozyme [a solution in 10 mM Tris-HCl (pH 8)], and further of 5 ml of a solution of 0.3% Triton ×100–187.5 mM EDTA (pH 8.0)-150 mM Tris-HCl (pH 8.0), the mixture was left at the room temperature for 15 minutes, well suspended, and centrifuged to obtain a cell extraction supernatant with a GIF activity.

(3) Purification and Identification of IL-1α Derivative

The product was purified by the chromatography procedure in the same manner as in Reference Example 1, (3) and (4) to obtain concentrated pure product. Isoelectric point, amino acid composition, and amino acid sequence were determined on this product to confirm that it was a polypeptide having an IL-1β amino acid sequence of from 24th to 153rd of SEQ ID No. 3.

Reference Example 6

Preparation of IL-1β derivative (1-82)

p trp GIF-α was digested with restriction endonuclease Pvu II to cut out a DNA fragment of about 2.9 kbp containing a region encoding an amino acid sequence of from 1st to 82nd amino acid residues of IL-1β. The DNA fragment was isolated and purified by agarose gel electrophoresis.

On the other hand, the 5' terminal of Xba I linker (5'-CTCTAGAG-3') was phosphorylated with T4 polynucleotide kinase and linked with the above DNA fragment by using T4 DNA ligase. The DNA was digested with restriction endonucleases Cla I and Xba I and subjected to agarose gel electrophoresis to isolate and purify a 250 bp DNA fragment.

Furthermore, plasmid pTM1 was digested with restriction endonuclease BamHI and the restriction endonuclease Bam HI cleavage site was made blunt by DNA polymerase (Klenow fragment). This DNA fragment was linked with Xba I linker (5'-CTCTAGAG-3') which had been phosphorylated with T4 polynucleotide kinase by using T4 DNA ligase. The DNA was digested with restriction endonucleases Cla I and Xba I and the fragment containing the trp promoter was isolated and purified by agarose gel electrophoresis.

This DNA fragment and the 250 bp DNA fragment previously obtained were linked by using T4 DNA ligase and transformed into *Escherichia coli* HB 101. The target transformant was selected by the restriction endonuclease analysis of the plasmid DNA obtained by the boiling method.

(2) Cultivation of the Transformant

The above transformant was cultivated and treated in the same manner as Reference Example 5 to obtain a cell extract supernatant having a GIF activity.

(3) Purification and Identification of IL-1α Derivative

Isoelectric point, amino acid composition, and amino acid sequence were determined on the concentrate purified product to confirm that it was a polypeptide having IL-1β amino acid sequence of from 1st to 82nd of SEQ ID No. 3.

Reference Example 7

36D•141S•IL-1α was obtained according to the method described in European Patent Publication No. 237073. Also, 71S•IL-1β was obtained according to the method described in European Patent Publication No. 237967.

Example 1

Preparation of drug for the treatment of liver diseases

Human serum albumin (HSA) was added to a solution of IL-1α derivative (IL-1α•Delta(1-14)•36D•141S), obtained in Reference Example 2, in a physiological saline ($1\times10^6$ unit of GIF activity per ml) to a concentration of 0.5%, filtered (a 0.22 μm membrane filter was used), sterilizingly charged into 1 ml vials, and freeze-dried to prepare an injection preparation.

The injection preparation is used by dissolving it in 1 ml of distilled water each time it is injected.

Example 2

Test for pharmacological effects

The example concerns a test for verifying the pharmacological effects of effective components of the drug for curing liver diseases of the present invention.

The polypeptide used in the test was rat IL-1α obtained by the method described in Japanese Patent Laid-open (kokai) No. 168286/1989. The reason for the use of the rat IL-1α was that if human IL-1α was administered to rats for a long period of time, problems such as production of antigens or the like might arise. The rat (rat with hereditary hepatitis, LEC rat; Long-Evans with cinnamon-like coat color) used in the experiment was developed and established in Experimental Animal Center, Hokkaido University in 1987. The rat was an Long-Evans type spontaneous mutant. It was an animal model, of which 100% got hepatitis in 16–17 weeks after born, 70–80% among them got chronic hepatitis, which developed into hepatic cancer within 1 to 1.5 years [Yoshida, M. C., et al., J. Hered. 78, 361–365 (1987)]. In this experiment, LEC rat was made into specific-pathogen-free (such a rat hereinafter is abbreviated as "SPF-LEC/otk").

Rats, SPF-LEC/otk, were divided into a solvent (rat serum albumin 100 μg/ml) dosing group (one male, and two females) and a rat IL-1α (10 μg/kg/day) dosing group (3 females). Each chemical was subcutaneously administered to animals of the two groups for a period of time from 8-week age to 20-week age, each week consisting of consecutive 5 days during which the chemical was administered and 2 days for which the chemical was not administered. The animals were grown under the conditions of room temperature ($23°\pm2°$ C.) and RE $55\pm5\%$, while feed (CRF-1, a product of Oriental Yeast Co.) and water were freely given.

0.5 ml of blood was sampled from caudal vein of animals once two weeks, serum was separated from the blood (3,000 rpm×5 minutes) to measure GPT, GOT, and Gamma-glutamyl transferase (Gamma-GT). For the enzyme analysis, kits for $GPT_{opt}$•monoest, $GOT_{opt}$•monotest, and Gamma-GT•monotest (manufactured by Boehringer-Manheim Co.) were used. Body weights were measured once a week.

The results are shown in FIGS. 1 and 2.

In the figures, the age by week of the LEC liver disease model was administered were plotted along the abscissa to show GPT measurement results (FIG. 1, unit: IU/l) and GOT measurement results (FIG. 2, unit: IU/l). (A), (B), and (C) in each drawing represent rats belonging to the rat IL-1α (10 μg/kg/day) dosing group, and (D), (E), and (F) those belonging to the solvent (rat serum albumin 100 μg/ml) dosing group.

Based on the results of FIGS. 1 and 2, a rapid increase in GPT and GOT activities was recognized at around 16-week age on all animals in the solvent dosing group, while the GPT and GOT activities were in a normal range in rats belonging to the rat IL-1α dosing group all through the period during which the drug was administered, i.e., up to 20-week age.

Weights and changes in symptoms of rats from each group during 16 to 20-week age in the test are summarized in Table 6.

TABLE 6

| Tested Group | Period of 16 to 20-week age |
| --- | --- |
| Solvent dosing group | Choloplania developed in all animals. Weight decreased. 2 of 3 animals were d |
| IL-1α dosing group | No special changes in all animals. |

As summarized in Table 6, choloplania and weight decrease which are typical symptoms in hepatitis were observed in animals of the solvent dosing group and 2 animals were dead, while in the IL-1α dosing group no such symptoms were observed and all animals were alive.

No remarkable tendency were observed on gamma-GT in the both dosing groups.

From the above results, IL-1 was proven to exhibit a remarkable liver disease inhibitory activity in model rats with hereditary hepatitis.

Example 3

Test for pharmacological effects (Dose dependency)

A solvent (rat serum albumin 100 μg/ml) and rat IL-1α (1 μg/kg or 10 μg/kg) were continuously administered to female SPF-LEC/otk rats by subcutaneous injection, beginning from 8-week of age; everyday for consecutive 5 days followed by 2 days for which the dosing was suspended. Three animals were used for each group. Animals were fed in the same manner as in Example 2, weighed once a week from 8 weeks of age, and the GPT and GOT activities in serum were measured once two weeks, to serve the results as a hepatitis marker.

150 μl of blood was collected from caudal vein of rats in a heparin-treated capillary and centrifuged at 2,500 rpm for 5 minutes to separate plasma. GPT and GOT values in plasma were measured by $GPT_{opt}$•monotest (Boehringer-Manheim-Yamanouchi Co.) and $GOT_{opt}$•monotest (Boehringer-Manheim-Yamanouchi Co.).

Figure 4:
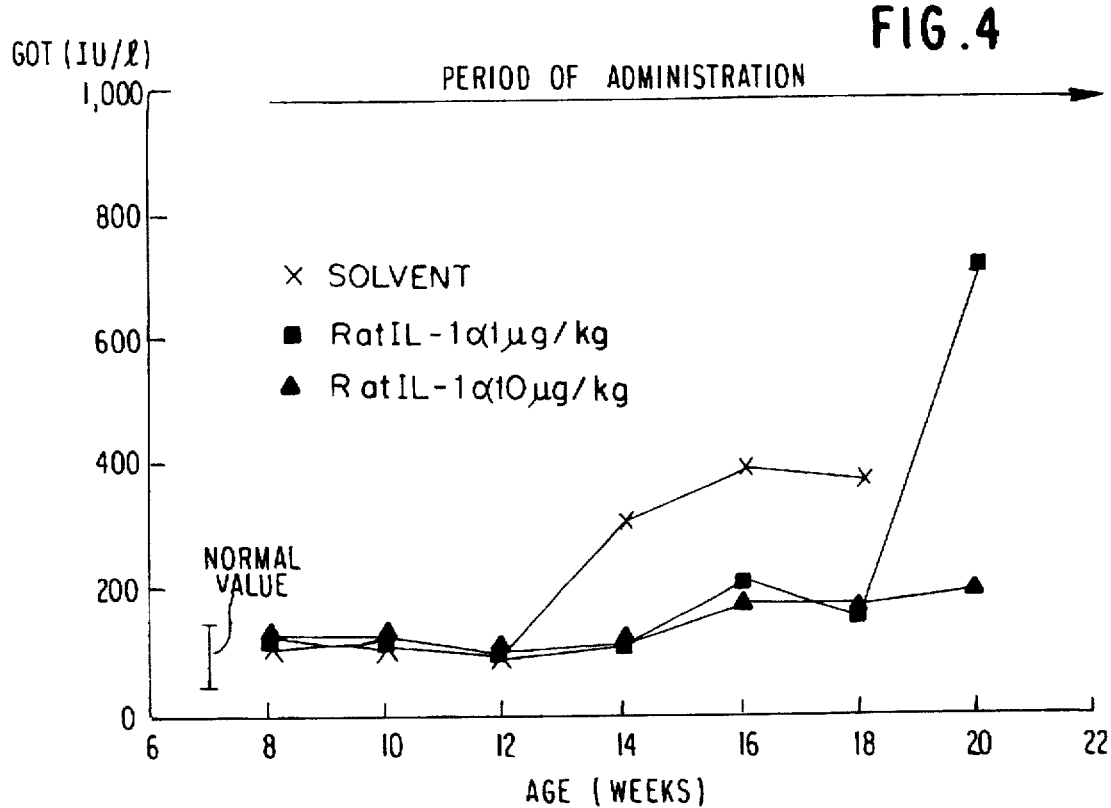
FIG. 4 is a graph showing the changes in the GOT activity as a result of pharmacological tests conducted on LEC hepatitis model rats according to Example 3.

The results were shown in FIGS. 3 and 4, which shows a rapid increase in GPT and GOT activities at around 16-week age in the animals in the solvent dosing group. Animals of that group were dead at 18-week age. On the other hand, there have been no great increase in the GPT and GOT activities observed in the both groups to which 1 μl/kg or 10 μl/kg of the rat IL-1α was administered. The effects were particularly remarkable in the group to which 10 μl/kg was dosed.

Industrial Applicability

A drug for preventing and curing liver disease can be provided by the present invention.

---

We claim:

1. A method for inhibiting the development of hepatitis, comprising the step of administering, to a subject suffering from a disorder associated with development of hepatitis, one or more doses of a therapeutic composition comprising Interleukin-1 (IL-1) protein, wherein the administration of IL-1 protein is effective to inhibit the development of abnormal levels of one or more markers associated with hepatitis.

2. The method as claimed in claim 1, wherein said Interleukin-1 protein is IL-1α.

3. The method as claimed in claim 1, wherein said Interleukin-1 protein is IL-1β.

4. The method as claimed in claim 1, wherein said Interleukin-1 protein is selected from the group consisting of 16G•36D•141S•IL-1α, 36D•141S-IL-1α, Δ(1–14)•36D•141S-IL-1α, Δ(1–15)•IL-1α and Δ(1–15)•36D•141S•IL-1α.

5. The method as claimed in claim 1, wherein said Interleukin-1 protein is selected from the group consisting of (25–153)•IL-1β, (1-82)•IL-1β and 71S•IL-1β.

6. The method as claimed in claim 1, wherein the disorder is associated with the development of chronic hepatitis.

7. The method as claimed in claim 1, wherein the disorder is associated with the development of acute hepatitis.

8. The method as claimed in claim 1, wherein said IL-1 protein is administered in an amount of from about 0.01 μg to 10 mg per day.

* * * * *